US010633539B2

(12) United States Patent
Phukan et al.

(10) Patent No.: US 10,633,539 B2
(45) Date of Patent: Apr. 28, 2020

(54) COMPOSITION COMPRISING ORGANOSILOXANE NANO LATEX AND PREPARATION OF ORGANOSILOXANE NANO LATEX

(71) Applicant: Momentive Performance Materials Inc., Waterford, NY (US)

(72) Inventors: Monjit Phukan, Bangalore (IN); Anubhav Saxena, Bangalore (IN); Shrutisagar D. Haveli, Maharashtra (IN); Sandeep Naik, Maharashtra (IN); Amar Pawar, Elmsford, NY (US); Dian Liu, Shanghai (CN); Yun Huang, Shanghai (CN)

(73) Assignee: Momentive Performance Materials Inc., Waterford, NY (US)

( * ) Notice: Subject to any disclaimer, the term of this patent is extended or adjusted under 35 U.S.C. 154(b) by 65 days.

(21) Appl. No.: 15/066,395

(22) Filed: Mar. 10, 2016

(65) Prior Publication Data

US 2017/0260393 A1 Sep. 14, 2017

(51) Int. Cl.
| | |
|---|---|
| *C08F 290/14* | (2006.01) |
| *C08L 83/06* | (2006.01) |
| *C08G 77/442* | (2006.01) |
| *A61K 8/895* | (2006.01) |
| *C08F 290/06* | (2006.01) |
| *C08L 83/10* | (2006.01) |
| *A61K 8/89* | (2006.01) |
| *A61Q 1/02* | (2006.01) |
| *A61Q 1/10* | (2006.01) |
| *A61Q 17/04* | (2006.01) |
| *A61Q 15/00* | (2006.01) |
| *A61Q 19/00* | (2006.01) |
| *C08G 77/14* | (2006.01) |

(52) U.S. Cl.
CPC ............... *C08L 83/06* (2013.01); *A61K 8/89* (2013.01); *A61K 8/895* (2013.01); *A61Q 1/02* (2013.01); *A61Q 1/10* (2013.01); *A61Q 17/04* (2013.01); *C08F 290/062* (2013.01); *C08F 290/142* (2013.01); *C08F 290/148* (2013.01); *C08G 77/442* (2013.01); *C08L 83/10* (2013.01); *A61K 2800/413* (2013.01); *A61K 2800/54* (2013.01)

(58) Field of Classification Search
None
See application file for complete search history.

(56) References Cited

U.S. PATENT DOCUMENTS

| | | | |
|---|---|---|---|
| 4,962,165 A | 10/1990 | Bortnick et al. | |
| 5,462,988 A | 10/1995 | Doi et al. | |
| 5,482,994 A | 1/1996 | Liles et al. | |
| 5,629,388 A | 5/1997 | Himelrick et al. | |
| 5,731,379 A | 3/1998 | Kennan et al. | |
| 5,840,813 A | 11/1998 | Gornowicz et al. | |
| 6,207,782 B1 | 3/2001 | Czech et al. | |
| 6,420,480 B1 | 7/2002 | Ozdeger | |
| 6,433,077 B1 | 8/2002 | Craig et al. | |
| 7,687,574 B2 | 3/2010 | Lu et al. | |
| 7,833,541 B2 | 11/2010 | Lu et al. | |
| 7,887,785 B2 | 2/2011 | Rojas-Wahl et al. | |
| 7,998,583 B2 | 8/2011 | Minge et al. | |
| 8,178,637 B2 | 5/2012 | Parker et al. | |
| 8,653,214 B2 | 2/2014 | Venzmer et al. | |
| 8,835,583 B2 | 9/2014 | Saxena et al. | |
| 8,901,265 B2 | 12/2014 | Masubuchi et al. | |
| 9,018,332 B2 | 4/2015 | Okawa et al. | |
| 2002/0035186 A1 | 3/2002 | Ona et al. | |
| 2005/0176894 A1 | 8/2005 | Jeong et al. | |
| 2005/0277563 A1 | 12/2005 | Ferguson et al. | |
| 2006/0281834 A1 | 12/2006 | Lee et al. | |
| 2011/0150818 A1 | 6/2011 | Canfield et al. | |
| 2012/0237464 A1 | 9/2012 | Ahn et al. | |

(Continued)

FOREIGN PATENT DOCUMENTS

| | | |
|---|---|---|
| EP | 0 614 924 A1 | 9/1994 |
| EP | 0 852 239 B1 | 7/1998 |
| EP | 0 853 093 A1 | 7/1998 |

(Continued)

OTHER PUBLICATIONS

International Search Report and Written Opinion from PCT/US2017/021510 dated May 26, 2017.

*Primary Examiner* — Jeffrey T. Palenik
(74) *Attorney, Agent, or Firm* — Joseph S. Ostroff

(57) ABSTRACT

A hydrophobic hybrid organosiloxane nano latex is provided as the copolymerizate of:

(a) organosiloxane monomer of the general formula
$M_a M^v_b D_c D^v_d T_e T^v_f Q_g$
wherein:
$M=R_1 R_2 R_3 SiO_{1/2}$,
$M^v=R_4 R_5 R_u SiO_{1/2}$,
$D=R_6 R_7 SiO_{2/2}$,
$D^v=R_8 R_u SiO_{2/2}$,
$T=R_9 SiO_{3/2}$,
$T^v=R_u SiO_{3/2}$, and
$Q=SiO_{4/2}$
in which $R_1$, $R_2$, $R_3$, $R_4$, $R_5$, $R_6$, $R_7$, $R_8$ and $R_9$ each independently is hydrogen, a hydroxyl group, a hydrocarbyl group having up to 100 carbon atoms and optionally containing at least one hetroatom; $R_u$ is a free-radical polymerizable group; subscripts a, b, c, d, e, f and g each independently range from 0 to 10,000 subject to the limitation that b+d+f is at least 1, p, q and r are integers independently selected from 0 to 100 and subscript h is 0 or 1; and, (b) monomer possessing a group which is free-radical copolymerizable with group $R_u$ of organosiloxane monomer (a).

27 Claims, No Drawings

(56) References Cited

U.S. PATENT DOCUMENTS

2013/0142743 A1* 6/2013 Cavazzuti ............ A61K 8/8194
424/64
2013/0172427 A1* 7/2013 Saxena ................ C09D 183/08
514/772.1

FOREIGN PATENT DOCUMENTS

| EP | 1178150 | A1 | 2/2002 | |
|----|---------|----|--------|---|
| EP | 1772500 | A2 | 4/2007 | |
| EP | 1772500 | B1 * | 3/2010 | ........... C09D 183/00 |

* cited by examiner

COMPOSITION COMPRISING ORGANOSILOXANE NANO LATEX AND PREPARATION OF ORGANOSILOXANE NANO LATEX

FIELD OF THE INVENTION

The present invention relates to organosiloxane latexes, their preparation and personal care products containing same.

BACKGROUND OF THE INVENTION

Organosiloxanes of various kinds are often incorporated in personal care compositions, e.g., skin and hair care products and cosmetics, in order to impart or augment one or more aesthetic, sensory and/or functional properties that consumers have come to regard as highly desirable. For example, organosiloxanes may be included in the formulations of skin care products such as lotions, skin cleansers, body washes, razor moisturizing strips, shaving gels, bar soaps, antiperspirants, deodorants, sunscreens, lip balm, and the like, in order to impart a soft and satisfying feel to these products as they are applied.

Hair care products such as shampoo, conditioners, hair colorants, depilatories, and the like, may be formulated with organosiloxanes to convey an impression of quality and luxuriousness to consumers.

Similarly, cosmetic compositions such as foundation, concealer, beauty balm, blush, mascara, lipstick, lip gloss, and the like, may also contain organosiloxanes to enhance their sensory effects as perceived by consumers.

SUMMARY OF THE INVENTION

In accordance with the present invention, there is provided a hydrophobic hybrid organosiloxane nano latex comprising the copolymerizate of (a) organosiloxane monomer of the general formula
wherein:
$M = R_1R_2R_3SiO_{1/2}$,
$M^v = R_4R_5R_uSiO_{1/2}$,
$D = R_6R_7SiO_{2/2}$,
$D^v = R_8R_uSiO_{2/2}$,
$T = R_9SiO_{3/2}$,
$T^v = R_uSiO_{3/2}$, and
$Q = SiO_{4/2}$
in which $R_1$, $R_2$, $R_3$, $R_4$, $R_5$, $R_6$, $R_7$, $R_8$, and $R_9$ each independently is hydrogen, a hydroxyl group, a hydrocarbyl group having up to 100 carbon atoms and optionally containing at least one hetroatom; $R_u$ is a free-radical polymerizable group; subscripts a, b, c, d, e, f and g each independently range from 0 to 10,000 subject to the limitation that b+d+f is >1; and, (b) monomer possessing a group which is free-radical copolymerizable with group $R_u$ of organosiloxane monomer (a).

The hydrophobic character of the organosiloxane nano latex herein makes this latex a particularly desirable component of personal care products such as those mentioned above where resistance to water wash-off, a capability that equates to longer wearability, is a much sought-after functional property. Without wishing to be bound, the improved resistance to water wash-off of the hydrophobic hybrid organosiloxane nano latex is thought to be attributable at least in part to its superior film-forming behavior and/or its greater hydrophobicity.

DETAILED DESCRIPTION OF THE INVENTION

In the specification and claims herein, the following terms and expressions are to be understood as indicated.

The singular forms "a," "an," and "the" include the plural, and reference to a particular numerical value includes at least that particular value, unless the context clearly dictates otherwise.

All methods described herein may be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

The terms, "comprising," "including," "containing," "characterized by," and grammatical equivalents thereof are inclusive or open-ended terms that do not exclude additional, unrecited elements or method steps, but will also be understood to include the more restrictive terms "consisting of" and "consisting essentially of."

It will be understood that any numerical range recited herein includes all sub-ranges within that range and any combination of the various endpoints of such ranges or sub-ranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

The expression "hydrocarbyl group" means any hydrocarbon from which one or more hydrogen atoms has been removed and is inclusive of alkyl, alkenyl, alkynyl, cyclic alkyl, cyclic alkenyl, cyclic alkynyl, aryl, aralkyl and arenyl and may contain heteroatoms.

The term "alkyl" means any monovalent, saturated straight, branched or cyclic hydrocarbon group; the term "alkenyl" means any monovalent straight, branched, or cyclic hydrocarbon group containing one or more carbon-carbon double bonds where the site of attachment of the group can be either at a carbon-carbon double bond or elsewhere therein; and, the term "alkynyl" means any monovalent straight, branched, or cyclic hydrocarbon group containing one or more carbon-carbon triple bonds and, optionally, one or more carbon-carbon double bonds, where the site of attachment of the group can be either at a carbon-carbon triple bond, a carbon-carbon double bond or elsewhere therein. Examples of alkyls include methyl, ethyl, propyl and isobutyl. Examples of alkenyls include vinyl, propenyl, allyl, methallyl, ethylidenyl norbornane, ethylidene norbornyl, ethylidenyl norbornene and ethylidene norbornenyl. Examples of alkynyls include acetylenyl, propargyl and methylacetylenyl.

The expressions "cyclic alkyl", "cyclic alkenyl", and "cyclic alkynyl" include bicyclic, tricyclic and higher cyclic structures as well as the aforementioned cyclic structures further substituted with alkyl, alkenyl, and/or alkynyl groups. Representative examples include norbornyl, norbornenyl, ethylnorbornyl, ethylnorbornenyl, cyclohexyl, ethylcyclohexyl, ethylcyclohexenyl, cyclohexylcyclohexyl and cyclododecatrienyl.

The term "aryl" means any monovalent aromatic hydrocarbon group; the term "aralkyl" means any alkyl group (as defined herein) in which one or more hydrogen atoms have been substituted by the same number of like and/or different aryl (as defined herein) groups; and, the term "arenyl" means any aryl group (as defined herein) in which one or more hydrogen atoms have been substituted by the same number of like and/or different alkyl groups (as defined herein). Examples of aryls include phenyl and naphthalenyl. Examples of aralkyls include benzyl and phenethyl. Examples of arenyls include tolyl and xylyl.

The term "hetroatom" means any of the Group 13-17 elements except carbon and includes, for example, oxygen, nitrogen, silicon, sulfur, phosphorus, fluorine, chlorine, bromine and iodine.

As previously stated, in organosiloxane monomer (a), $R_1$-$R_9$ each independently is hydrogen, a hydroxyl group or a hydrocarbyl group having up to 100 carbon atoms and optionally containing at least one hetroatom.

In one embodiment, hydrocarbyl group(s), where present, contain up to 60 carbon atoms, in another embodiment up to 30 carbon atoms and in yet another embodiment up to 20 carbon atoms.

Useful hydrocarbyl groups include alkyl groups examples of which are methyl, ethyl, n-propyl, isopropyl, n-butyl, isobutyl, tert-butyl, n-pentyl, isopentyl, neopentyl and tert-pentyl; hexyl such as n-hexyl; heptyl such as n-heptyl; octyl such as n-octyl, isooctyl and 2,2,4-trimethylpentyl; nonyl such as n-nonyl; decyl such as n-decyl; and cycloalkyl, such as cyclopentyl, cyclohexyl, cycloheptyl and methylcyclohexyl. Examples of alkenyl groups include vinyl, propenyl, allyl, methallyl, cyclohexenyl, norbornenyl, ethylnorbornenyl, ethylidenyl norbornane, ethylidene norbornyl, ethylidenylnorbornene and ethylidene norbornenyl. Examples of alkynyl groups include acetylenyl, propargyl and methylacetylenyl. Examples of aryl groups include phenyl, naphthyl; o-, m- and p-tolyl, xylyl, ethylphenyl and benzyl.

As previously stated, in organosiloxane monomer (a), $R_u$ is a free-radical polymerizable group. Thus, for example, each $R_u$ may independently be selected from among alkenyl, alkynyl, acrylate, acrylamide, methacrylate, methacrylamide, and the like, groups.

In one embodiment, free-radical polymerizable group Ru of monomer (a) may be an ethylemically unsaturated group of one of Formulas I, II(a), II(b) and II(c) as follows:

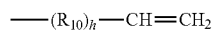

Formula I

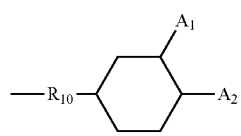

Formula II(a)

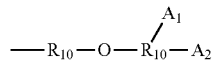

Formula II(b)

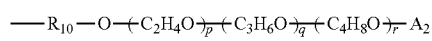

Formula II(c)

wherein:

each $R_{10}$ is independently selected from linear or branched alkyl groups of up to 10 carbon atoms and optionally containing at least one heteroatom; $A_1$ and $A_2$ each is an olefincially unsaturated group capable of undergoing free radical addition with monomer (b), infra, and, subscripts p, q and r each independently range from 0 to 100 and subscript h is 0 or 1.

In one embodiment of Formulas II(a), II(b) and/or II(c), $A_1$ and/or $A_2$ are independently a group of the Formula III:

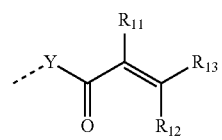

Formula (III)

wherein $R_{11}$, $R_{12}$ and $R_{13}$ are independently selected from hydrogen and hydrocarbyl group of up to 5 carbon atoms, Y is nothing or a linker group chosen from divalent aliphatic, cycloaliphatic or aromatic hydrocarbon groups of 2 to 16 carbons and optionally containing at least one heteroatom.

Examples of useful monomers (a) include vinyl functional polysilicone, hydroxy functional polysilicone acrylates, organo modified silicone (meth)acrylates, organo modified silicone (meth)acrylamides and its derivatives.

Monomer (b) is any monomer possessing a group which is free-radical copolymerizable with group $R_u$ of organosiloxane monomer(s) (a). In some embodiments, a single monomer (b) is copolymerized with monomer(s) (a) and in other embodiments, two or more monomers (b) are copolymerized with monomer(s) (a).

Examples of useful monomers (b) are acrylic acid, methacrylic acid, their esters and their amide derivatives such as methylacrylate, bultylacrylate, propylacrylate, N,N-dimethylacrylamide, N-isopropyl acrylamide, 2-ethylhexyl acrylate, cyclohexyl acrylate, vinlylacrylate, allylacrylate, hydroxyethyl acrylate, perfluoroethyl acrylate, isobornyl acrylate, lauryl arylate, phenoxyethyl acrylate, tetraethylene glycol diacrylate, tripropylene glycol diacrylate, acrylamide, methacrylamide, acrylated silane, methacrylated silane, methacryloxyl silane, 2-hydroxyethylmethacrylate, 3-[tris(trimethylsiloxy)silyl]propyl methacrylate, acrylate and methacrylate functional carbosilanes, hexafunctional urethane acrylates, dipentaerythritol pentaacrylate, ethoxylated pentaerythritol tetraacrylate, di-trimethylolpropane tetraacrylate, pentaerythritol triacrylate, trimethylolpropane triacrylate, ethoxylated trimethylolpropane triacrylate, butanediol diacrylate, tripropylene glycol diacrylate, trimethylolpropane trimethacrylate, oligofunctional urethane acrylates, tetraacrylate monomer, polyester acrylate oligomers, and combinations thereof.

Free-radical polymerizable monomer (b) may also be selected from among the ethylenically unsaturated monomers numerous ones of which are known in the art such as butadiene, styrene, ethyl styrene, divinyl benzene, N-vinyl pyrrolidone, N-vinyl lactam, vinyl halides, vinyl acetates, vinyl alcohols, vinyl ethers, allyl alcohols, allyl polyethers and others that can react with the Ru group of the organosiloxane of monomer (a).

The weight ratio of total monomer(s) (a) to total monomer(s) (b) can vary widely, i.e., in one embodiment a weight ratio of (a) to (b) of from 99.9 to 0.1, in another embodiment a weight ratio of (a) to (b) of from 99 to 1 and in yet another embodiment a weight ratio of (a) to (b) of from 95 to 5. The viscosity of the nano latex can vary widely, i.e., in one embodiment from 0.1 to 250 cps, in another embodiment from 0.5 to 230 cps and in yet another embodiment from 1 to 200 cps. Similarly, the particle size of the nano latex can be varied, e.g., in one embodiment the from 10 to 990 nm, in another embodiment from 20 to 800 nm and in yet another embodiment from 25 to 500 nm.

According to one embodiment of a free-radical emulsion copolymerization process by which the nano latex of the invention may be prepared, at least one free-radical polymerizable monomer (a) is combined with at least one free-radical polymerizable monomer (b), one or more surfactants and one or more co-stabilizers in an aqueous medium which is then emulsified under high shear mixing such as high speed mixing using rotor stator mixing systems of 5,000 to 50,000 rpm, high pressure homogenization utilizing pressures ranging from 10 to 2000 bar, sonication of 0.1 to 16 kW and combinations thereof to produce an emulsion in which the oil phase has a particle size of from 10 to 990 nm. Upon addition of one or more free radical initiators to the emulsion, copolymerization is conducted under conditions including a temperature of from 1 to 200° C., preferably from 15 to 150° C. and more preferably from 30 to 100° C. for a reaction time of from 1 min to 48 hrs, preferably from 5 mins to 48 hrs and more preferably from 15 mins to 24 hrs. Stirring condition will depend on the reaction conditions, the composition of the reaction medium and the stirring method to provide the hydrophobic hybrid organosiloxane nano latex herein.

In one embodiment, the hydrophobic hybrid organosiloxane nano latex exhibits as a measure of its hydrophobicity a contact angle of at least 50°, preferably at least 60°, and more preferably at least 70°, such manifesting itself as resistance to water wash-off, a highly desirable property for many types of personal care products such as sunscreens, wash-proof mascaras, eye-liners, lip colors, liquid foundations, and the like.

In one embodiment, the concentration of surfactant comprises 0.01 to 25 wt %, preferably 0.05 to 20 wt % and more preferably 0.1 to 10 wt % and the concentration of co-stabilizer comprises 0.01 to 20 wt %, preferably 0.05 to 10 wt % and more preferably 0.1 to 5 wt %.

In another embodiment of free-radical emulsion copolymerization process herein, a mini-emulsion procedure is employed which, following copolymerization, results in a hydrophobic hybrid organosiloxane nano latex that upon drying provides a soft film with good physical integrity. This process includes the following steps:

step 1: dispersing a uniform mixture of monomers (a) and (b) and co-stabilizer(s), hereafter referred to as the oil phase, within an aqueous phase containing 1-10 weight percent of surfactant(s) or mixture of surfactant(s) and co-stabilizer(s) with respect to the oil phase to form a coarse emulsion with a particle size ranging from 0.1 to 990 nanometer;

step 2: subjecting the coarse emulsion from step 1 to high energy mixing, for example, employing a high-pressure homogenizer, micro-fluidizer or ultra-sonic mixer, at from 1 to 80° C. to provide a mini-emulsion in which the oil phase has a particle size ranging from 10 to 990 nm and improved stability over that of the coarse emulsion of step 1; and, step 3: copolymerizing monomers (a) and (b) in the mini-emulsion of step 2 by adding one or more suitable water-soluble and/or oil-soluble free radical initiators at a temperature of from 10 to 90° C.

The surfactant(s) can be selected from among the anionic, cationic, zwitterionic and non-ionic surfactants and their combinations. The co-stabilizers can be selected, for example, from compounds having limited water solubility such as dodecane, cetyl alcohol, cetostearyl alcohol and combinations thereof.

In one embodiment, the surfactants can be, for example, the alkali metal salts of long chain alkyl sulfates and sulfonates such as dodecyl-1 acid sulfate, tetradecyl-1 acid sulfate, octadecyl-1 acid sulfate, dodecane-1-sulfonic acid, tetradecane-1-sulfonic acid, hexadecane-sulfonic acid and octadecane-sulfonic acid, and salts of long chain sulfonated paraffinic hydrocarbons and their combinations.

The initiator(s) can be, for example, hydrogen peroxide, ammonium persulfate, potassium persulfate, sodium persulfate, the organic peroxides, azo compounds and their combinations. The initiator(s) may also be composed of co-initiators such as Fe, $Cr^{2+}$, $V^{2+}$, $Ti3+$, $Co^{2+}$, $Cu^+$ and the like. The initiator is added to the emulsion to commence the copolymerization of monomers (a) and (b) therein. Depending on the nature of the selected initiator, copolymerization temperatures of from 40° to 100° C. with reaction times of from 1 to 10 hrs are generally suitable.

Optional Components

The organosiloxane latex composition of the invention may also contain one or more optional components such as any of the ingredients of known and conventional personal care products employed in the customary amounts. Among these ingredients may be mentioned other silicone, surfactant, emulsifier, solvent such as linear and cyclic siloxane, organic estes, alkane such as isododecane, isohexadencane, emollient, moisturizer, humectant, pigment, colorant, fragrance, preservative, antioxidant, biocide, biostat, antiperspirant, exfoliant, hormone, enzyme, medicinal, vitamin substance, hydroxy acid, retinal, retinol derivative, niacinamide, skin lightening agent, salt, electrolyte, alcohol, polyol, ester, scattering and/or absorbing agent for ultraviolet radiation, botanical extract, peptide, protein, organic oil, gum, saccharide, oligosaccharide, polysaccharide, derivative, wax, film former, thickening agent, particulate filler, plasticizer, humectant, occlusive, sensory enhancer, resin and optically active particle. These compounds may be added before, during or after polymerization of the organosiloxane.

Personal Care Uses

The hydrobic hybrid organosiloxane nano latex herein can improve the wear resistance and sensory properties of a broad range of personal care products, for example, deodorants, antiperspirants, antiperspirant/deodorants, stick and roll-on products, skin lotions, moisturizers, toners, cleansing products, styling gels, hair dyes, hair color products, hair straighteners, nail polish, nail polish remover, sunscreens, anti-aging products, lipsticks, lip balms, lip glosses, foundations, face powders, eye liners, eye shadows, blushes, makeup, beauty balms, mascaras, moisturizing preparations, foundations, concealers, body and hand preparations, skin care preparations, face and neck preparations, fragrance preparations, soft focus applications, night and day skin care preparations, tanning preparations, hand liquids, non-woven applications for personal care, baby lotions, facial cleansing products, hair cuticle coats, gels, foam baths, body washes, scrubbing cleansers, controlled-release personal care products, hair shampoos, hair conditioners, hair sprays, skin care moisturizing mists, skin wipes, pore skin wipes, pore cleaners, blemish reducers, skin exfoliators, skin desquamation enhancers, skin towelettes and cloths, depilatory preparations, personal care lubricants, nail coloring preparations and drug delivery systems for topical application of medicinal compositions that are to be applied to the skin.

In the examples that follow, the nano latex of the invention is produced by a process that includes high pressure homogenization and emulsion copolymerization. High pressure homogenization results in a mini-emulsion in which the oil phase possesses a narrow range of nanometer size and, following copolymerization, provides a more stable latex, i.e., one which is substantially free of coagulates and therefore one having improved shelf life. Films obtained from the hydrophobic hybrid organosiloxane nano latex herein are typically transparent and glossy, such being highly desirable properties for many types of personal care products including skin care creams and lotions for sun protection, moisturizers, anti-aging formulas; BB creams (beauty balms); hair care products such as hair creams, serums and styling products; color cosmetics such as lipsticks, nail paints, mascaras, foundations and lotions; and, cleansing products such as soaps, hand washes, shampoos and conditioners.

Comparative Example

Preparation of Hydrophilic Organosiloxane Latex of Example 1 of U.S. Pat. No. 6,207,782

A silicone polyether acrylate corresponding to Polysiloxane B of U.S. Pat. No. 6,207,782 was added slowly to the following water/surfactant mixture followed by initiator. The charges were as follow: 40 g silicone polyether acrylate, 156 g water, 4 g sodium lauryl sulfate and 0.2 g potassium persulfate. The emulsion was heated with agitation to 75-80° C. for 1 to 2 hours. After cooling to room temperature, solid sodium bicarbonate was added to adjust the pH of the hydrophilic latex-containing emulsion to neutral.

Examples 1-4

Preparation of Monomers(a): Trisiloxane Polyether Methacrylates

The preparation of trisiloxane polyether methacrylates (monomers(a)) was carried out in two steps. In the first step, hydrosilylation of hexamethyltrisiloxane [$(CH_3)_3SiO$—(H)Si($CH_3$)O—Si($CH_3$)$_3$] with 1.3 moles of allylpolyether of the general structure $H_2C$=C(H)$CH_2O(CH_2CH_2O)_n$H with n=0, 1, 3 and 8 was carried out in the presence of 10 ppm of Karstedt catalyst at 80° C. Each of the resulting silicone polyethers were then placed in individual three neck flasks and cooled to 0° C. after which 1.1 molar equivalent triethylamine was added. To each flask an equimolar amount of methacryl chloride (w.r.t. the hydroxyl groups) dissolved in 20 weight percent dry methylethylketone (MEK) was added dropwise. Once addition was complete, the reaction mixture was mixed for another three hours at ambient temperature. A white precipitate of triethylammonium chloride was removed by filtration and the filtrate was subjected to solvent removal at 40° C. at a reduced pressure of 10 mbar. The resulting four monomers (a) were determined by NMR to be methacrylated silicone polyethers containing some methacrylated polyether (n=0 in Example 1, n=1 in Example 2, n=3 in Example 3 and n=8 in Example 4).

Examples 5-15

Preparation of Hydrophobic Hybrid Organosiloxane Nano Latexes

A. Formation of Mini-Emulsions

Oil phases were prepared by dissolving the co-stabilizer cetyl alcohol in a mixture of butyl acrylate (BA) and methyl methacrylate (MMA). The methacrylated silicone polyethers of Examples 1-4 and were individually dissolved in an oil phase. Aqueous phases were prepared by sodium lauryl sulfate (SLS) in water. The oil and aqueous phases were mixed together by a magnetic stirrer for 10 min. at 1000 rpm to provide course mini-emulsions which were then either sonicated in a GE 601 Ultrasonicator for 5 min. at 0.5 seconds pulse or homogenized using a CAT X520 Rotar-Stator, 20 mm shaft, at 22,000 rpm to provide mini-emulsions. Temperature was maintained at 5° C. during sonication/homogenization to prevent or reduce polymerization.

The compositions of the mini-emulsion copolymerization reaction mixtures (all amounts in grams) are set forth in Table 1 below.

TABLE 1

Composition of Mini-Emulsion Copolymerization Reaction Mixtures

| Nano Latex Example | Organosiloxane Monomer(a) | Organosiloxane Monomer(a) | BA Monomer(b) | MMA Monomer(b) | SLS | Cetyl alcohol | Shearing Procedure |
|---|---|---|---|---|---|---|---|
| 5 | Ex. 1 | 6.25 | 8.875 | 8.875 | 1 | 1 | sonication |
| 6 | Ex. 2 | 6.25 | 8.875 | 8.875 | 1 | 1 | sonication |
| 7 | Ex. 3 | 12 | 6 | 6 | 1 | 1 | sonication |
| 8 | Ex. 3 | 6.25 | 8.875 | 8.875 | 1 | 1 | sonication |
| 9 | Ex. 4 | 6.25 | 8.875 | 8.875 | 1 | 1 | sonication |
| 10 | CoatOSil 3509[1] | 12 | 6 | 6 | 1 | 1 | sonication |
| 11 | CoatOSil 3509 | 6.25 | 8.875 | 8.875 | 1 | 1 | sonication |
| 12 | MMviQ[2] | 12 | 6 | 6 | 1 | 1 | sonication |
| 13 | MMviQ | 6.25 | 8.875 | 8.875 | 1 | 1 | sonication |
| 14 | divinyl PDMS[3] | 12 | 6 | 6 | 1 | 1 | sonication |
| 15 | divinyl PDMS | 6.25 | 8.875 | 8.875 | 1 | 1 | sonication |

[1]Acrylated siloxane polyalkyleneoxide copolymer (Momentive Performance Materials Inc.)
[2]Vinyl dimethylsiloxy silicate resin (Momentive Performance Materials Inc.)
[3]Vinyl end-capped polydimethylsiloxane (0.1 P · s) (Momentive Performance Materials Inc.)

B. Copolymerization of Mini-Emulsions to Provide Nano Latexes

Batch mini-emulsion copolymerizations were carried out in a 250 mL round bottom flask equipped with reflux condenser, stirrer and nitrogen inlet. Each mini-emulsion was added to a flask and kept under nitrogen atmosphere. When the temperature reached 70° C., potassium persulfate as initiator was injected into a flask. All four copolymerizations were carried out at 70° C. Samples were withdrawn at regular intervals with conversions being determined gravimetrically. The properties of the nano esters and the films obtained therefrom are set forth in Table 2.

TABLE 2

Properties of the Nano Latex Films

| Nano Latex Example | Conversion (%) | Particle Size (nm) $D_H$ | Film Properties | Viscosity (cps) |
|---|---|---|---|---|
| 5 | 96 | 110 | Semi-soft, dry, transparent | <10 |
| 6 | 96 | 122 | soft, dry, transparent | <10 |
| 7 | 98 | 110 | soft, dry, transparent | 105 |
| 8 | 97 | 110 | soft, dry, transparent | 107 |
| 9 | 96 | 96 | soft, dry, brittle | 285 |
| 10 | 98 | 110 | soft, dry, transparent | <10 |
| 11 | 98 | 122 | soft, dry, transparent | <10 |
| 12 | 92 | 300 | semisoft, dry, opaque | ~10 |
| 13 | 94 | 216 | semisoft, dry, opaque | ~10 |
| 14 | 95 | 360 | hard, dry, opaque | ~10 |
| 15 | 90 | 180 | soft, dry, transparent | ~10 |

Example 16

Preparation of Bis(Methacrylylpolyether)-Functionlized Polydimethylsiloxane, Mn~2400

A round-bottom flask equipped with a stirring bar, reflux condenser and nitrogen inlet was charged with 200 g of L-8620 (Silicone Polyether surfactant available from Momentive) and 123 g. of triethylamine and the flask flushed with nitrogen. The reaction mixture was placed under positive nitrogen pressure and 58 g (15% w/w) p-toluenesulfonyl chloride was charged in 4 equal batches in 15 minutes intervals. After completion of the reaction, excess p-toluenesulfonyl chloride was neutralized with 2.5 g of water (0.7% w/w) and 13 g. (3.5% w/w) of sodium bicarbonate. The reaction mixture was further stirred for one hour and filtered to yield a colorless liquid. The reaction was monitored by $^1$H NMR spectroscopy.

A round-bottom flask equipped with a stirring bar and reflux condenser was charged with 20 g bis(p-toluenesulphonylpolyether functionalized polydimethylsiloxane and 20 g cyclohexane. To this reaction mixture were added 200 ppm butylated hydroxyl toluene and 150 mg cetyl tertiary ammonium chloride as phase transfer catalyst. The reaction mixture was placed under positive nitrogen pressure. 1.7 g sodium methacrylate was added and the reaction mixture refluxed at 85° C. After completion of copolymerization, the reaction mixture was cooled to room temperature and filtered. The filtrate was stripped of cyclohexane solvent yielding a pale yellow liquid. The reaction was monitored by $^1$H NMR spectroscopy.

Example 17

Preparation of Bis(Methacrylyl)-Functionalized Polydimethylsiloxane, Mn~3500

A round-bottom flask equipped with a stirring bar, reflux condenser and addition funnel was charged with 48 g allyl glycidyl ether and 150 g bis(hydride)-terminated polydimethylsiloxane (Mn~3100). The reaction mixture was heated to 80° C. and 5 ppm of hexachloroplatinic acid (10% w/w in 2-propanol) was charged. After the initial exotherm, 350 g bis(hydride) terminated polydimethylsiloxane was charged in three intervals. During the final charge of hydride, an additional 5 ppm hexachloroplatinic acid was added. After the final exotherm, the temperature of the reaction mixture was raised to 90-95° C. and stirred for 2 hours. After completion of the reaction, excess allyl glycidyl ether was removed under vacuum yielding a straw yellow liquid. The reaction was monitored by $^1$H NMR spectroscopy A round-bottom flask equipped with a stirring bar and reflux condenser was charged with 375 g bis(allyl glycidyl ether)-functionalized polydimethylsiloxane, supra, 22 g methacrylic acid (5.4% w/w) and 300 ppm butylated hydroxytoluene. The reaction mixture was flushed with nitrogen and under positive pressure 1 g of triethylamine (0.25% w/w) was added. The reaction mixture was heated to 95° C. and stirred for 16-20 hours. After completion of the reaction, 100 ppm 2,2,6,6-tetramethyl-1-piperidinyloxy was added and the reaction was subjected to vacuum at 95° C. and 30 mbar to remove excess methacrylic acid. The reaction mixture was then stirred over Tulsion T-66 MP resin to remove traces of triethylamine. The reaction mixture was then filtered yielding a pale yellow viscous liquid. The reaction was monitored by $^1$H NMR spectroscopy Example 18

Preparation of Bis(Methacrylyl)-Functionlized Polydimethylsiloxane, Mn~2400

A round-bottom flask equipped with a stirring bar, reflux condenser and addition funnel was charged with 78 g. 4-vinyl-1-cyclohexene 1,2-epoxide and 500 g bis(hydride) terminated polydimethyl siloxane (Mn~2200). The reaction mixture was heated to 75° C. at which point 10 ppm of Karstedt catalyst (2% in xylene) was added and the reaction mixture further heated to 90-95° C. Hydride fluid was added drop wise to the mixture to prevent runaway reaction due to exotherm. After completion of the reaction, excess 4-vinyl-1-cyclohexene 1,2-epoxide was stripped off under vacuum yielding a straw yellow liquid. The reaction was monitored by $^1$H NMR spectroscopy.

A round-bottom flask equipped with stirring bar and reflux condenser was charged with 500 g of bis(4-vinyl-1-cyclohexene 1,2-epoxide)-functionalized polydimethylsiloxanes, supra, and heated to 75° C. At this point, 2,000 ppm titanium isopropoxide and 300 ppm butylated hydroxyltoluene were added to the reaction mixture which was further heated to 90-95° C. 42 g methacrylic acid was then added drop wise to the reaction mixture and the mixture stirred until completion of the reaction. The reaction product was cooled to ambient temperature and passed over Tulsion ACR-499 resin to remove traces of methacryle acid. The product was further filtered yielding a pale yellow viscous liquid. The reaction was monitored by $^1$H NMR spectroscopy.

Examples 19-28

Preparation and Copolymerization of Mini-Emulsions to Provide Nano Latexes

Individual oil phases were prepared by dissolving the acrylated organosiloxanes of Examples 16-18 as monomer (a), butyl acrylate as monomer (b) and cetyl alcohol as co-stabilizer. Individual aqueous phases were prepared by dissolving 70% sodium lauryl ether sulfate (SLES) in water. The oil phases were gradually added to the water phases under stirring at 500-600 rpm. Each of the resulting coarse emulsions were homogenized using a CAT X520 Rotarstator, 30 mm shaft at 15000 rpm or micro-fluidizer to provide mini-emulsions. The temperature was maintained at 15-20° C. to prevent or limit polymerization.

The components of the mini-emulsions are set forth in Table 3 as follows:

TABLE 3

Nano Latex Compositions

| Nano Latex Example | Organo-siloxane Monomer (a) | Organo-siloxane Monomer (a) | BA Monomer (b) | SLES (70%) | Cetyl Alcohol | Shearing Apparatus |
|---|---|---|---|---|---|---|
| 19 | Ex. 16 | 12 | 12 | 2.142 | 1 | Rotor-stator |
| 20 | Ex. 18 | 12 | 12 | 2.142 | 1 | Rotor-stator |
| 21 | Ex. 17 | 8 | 16 | 2.142 | 1 | Rotor-stator |
| 22 | Ex. 18 | 8 | 16 | 2.142 | 1 | Rotor-stator |
| 23 | Ex. 17 | 4.8 | 19.2 | 2.142 | 1 | Rotor-stator |
| 24 | Ex. 18 | 40 | 80 | 26.785 | 5 | Micro-fluidizer |
| 25 | Ex. 18 | 10 | 20 | 1.5 | 1 | Micro-fluidizer |
| 26 | Ex. 18 | 13.5 | 26.5 | 1.5 | 1 | Micro-fluidizer |
| 27 | Ex. 18 | 40 | 80 | 26.78 | 5 | Micro-fluidizer |
| 28 | Ex. 18 | 64 | 128 | 42.85 | 8 | Micro-fluidizer |

Copolymerization within each mini-emulsion was carried out in a round bottom flask equipped with a reflux condenser, stirrer and provided with positive nitrogen flow. Potassium persulfate as initiator was added to each mini-emulsion which was then heated to 65° C. Samples of each reaction mixture were drawn at regular intervals with conversions being determined gravimetrically.

TABLE 4

Physical Properties of Nano Latexes of Comp. Ex. 1 and Ex. 19-28 and Dried Films Obtained Therefrom

| Latex Example | Viscosity (cps) | Particle size (nm) | Film Properties |
|---|---|---|---|
| Comp. Ex. 1 | 25 | 10,000-100,000 | tacky and not self-standing |
| 19 | <10 | 142 | soft, tack-free, hazy |
| 20 | <10 | 183 | soft, tack-free, hazy |
| 21 | <10 | 163 | soft, tack-free, hazy |
| 22 | <10 | 163 | soft, tack-free, transparent |
| 23 | <10 | 142 | soft, tack-free, transparent |
| 24 | <10 | 132 | soft, tack-free, transparent |
| 25 | <50 | 137 | soft, tack-free, transparent |
| 26 | <100 | 127 | soft, tack-free, transparent |
| 27 | <10 | 135 | soft, tack-free, transparent |
| 28 | <10 | 150 | soft, tack-free, transparent |

The data in Table 4 demonstrates that the nano latexes of the invention have in most cases a lower viscosity than that of Comparative Example 1. Lower viscosity is advantageous for the manufacture of personal care compositions. In addition, the much lower particle size of all the nano latexes herein results in improved self-life stability and for most of them, improved transparency (lack of haziness) compared with that of Comparative Example 1. Such properties make nano latexes of the invention overall technically superior to the latex of Comparative Example 1 for cosmetic applications.

Example 29

Preparation of Methacrylated Silicone Emulsion 49.14 weight parts dimethiconol having a viscosity of about 0.7 Pa·s at 25° C. and 0.86 weight parts 3-(methacryloxy)propylmethyldiethoxysilane were mixed together and charged to an admixture of 4 weight parts ethoxylated cetearyl alcohol, 0.5 weight parts sodium cetearyl sulfate and 6 weight parts deionized water with increased charging rate and mixing speed to provide a stable emulsion followed by charging deionized water to the emulsion containing 50% oil. The pH was adjusted to 2 and neutralization until the internal viscosity no more than 6 Pa·s.

35 weight parts of the emulsion were heated to 80° C. to which was charged 0.05 parts of ammonium persulfate in 10 weight parts deionized water and a premix containing 8.75 weight parts methyl methacrylate, 8.75 weight parts butyl acrylate, 0.5 weight parts ethoxylated cetearyl alcohol and 5 weight parts of deionized water. The copolymerization reaction was carried out for 2 hours. Deionized water and preservative were charged to provide a methacrylated silicone emulsion having a copolymer content of 35 weight percent.

Example 30

Preparation of Functionalized Silicone/Lauryl Methacrylate Emulsion 49.67 weight parts dimethiconol having a viscosity of about 0.7 Pa·s at 25° C. 0.33 weight parts 3-(methacryloxy)propylmethyldiethoxysilane were mixed together and charged to an admixture of 4 weight parts PEG-40 stearate, 0.5 weight parts sodium cetearyl sulfate and 6 weight parts deionized water with increased charging rate and mixing speed to provide a stable emulsion, followed by charging deionized water to a emulsion containing 50% oil. The pH was adjusted to 2 and neutralization until the internal viscosity reached 3 Pa·s.

56 weight parts of the emulsion was heated to 80° C. to which was charged 0.035 weight parts ammonium persulfate in 10 weight parts deionized water and a premix containing 7 weight parts lauryl methacrylate, 0.5 weight parts PEG-40 stearate and 4 weight parts deionized water. The copolymerization reaction was carried out for 3 hours. Deionized water and preservative were charged to provide a functionalized silicone/LMA emulsion having a copolymer content of 35 weight percent.

The contact angles of dried films obtained from the latexes of Comparative Example 1, Examples 5 and 22 were measured by contact angle goniometry. Contact angle is a measurement of the hydrophobicity of a film and is indicative of the resistance to wash wash-off of a film and therefore of the nano latex from which the film is obtained. A film of latex polymer was prepared by drawing down a test latex on a glass substrate to provide a 200 μm wet film. The coated substrate was placed in an oven at 45° C. for 12 hrs. The dried coated substrate were then placed in a Rame Hart contact angle goniometer model 250. A 5 μL drop of distilled deionized water was transferred to the surface via a syringe. The water droplet was allowed to equilibrate for 1 minute and the contact angle was measured via the supplied software. The contact angle was determined as the angle which the leading edge of the drop exhibited relative to the coated glass substrate. The higher the angle the more hydrophobic the film-coated surface. The contact angles were as set forth in Table 5 below:

TABLE 5

Contact Angles of Dried Films

| Dried Film of Latex Polymer | Contact Angle |
|---|---|
| Comp. Ex. 1 | 39 |
| Ex. 5 | >102 |
| Ex. 22 | 75 |

As the data in Table 5 show, films formed from the latexes of Examples 5 and 22 exhibited much higher contact angles than the film formed from the latex of Comparative Example 1. Higher contact angles imply greater hydrophocity which as noted above equates to improved resistance of water wash-off of personal care products formulated with such latexes.

Example 31

Preparation of Functionalized Silicone/Acrylate/Styrene Emulsion 49.14 parts dimethiconol having a viscosity of about 0.55 Pa·s at 25 □ C and 0.86 parts 3-(methacryloxy)propyltrimethoxysilane were mixed together and charged to an admixture of 4 weight parts ethoxylated cetearyl alcohol, 0.5 weight parts sodium cetearyl sulfate and 6 weight parts deionized water with increased charging rate and mixing speed to provide a stable emulsion followed by charging deionized water to an emulsion containing 50% oil. The pH was adjusted to 2 and neutralization until the internal viscosity reached 6 Pa·s.

56 weight parts of the emulsion were heated to 80° C. to which was charged 0.035 parts of ammonium persulfate in 5 weight parts deionized water and a premix containing 5 weight parts butyl acrylate, 2 weight parts styrene, 0.5 weight parts ethoxylated cetearyl alcohol and 4 weight parts of deionized water. The copolymerization reaction was carried out for 3 hours. Deionized water and preservative were charged to provide a functionalized silicone/acrylate/styrene emulsion having a solids content of 48 weight percent.

Example 32

A sunscreen composition was prepared with the components and in the amounts (grams) set forth below in Table 6 (all amounts in weight percent):

TABLE 6

Sunscreen Composition

| Component | Ex. 31 |
|---|---|
| stearic acid | 3.63 |
| cetyl alcohol | 0.57 |
| dimethicone 350 cst | 0.00 |
| latex of Ex. 10 | 10.00 |
| trimethylsiloxysilicate | |
| C12-15 alkylbenzoate | 5.00 |
| caprylic capric triglyceride | 5.00 |
| octylmethoxycinnamate | 7.50 |
| octylsalicylate | 5.00 |
| oxybenzone | 6.00 |
| avobenzone | 3.00 |
| tetrasodium EDTA | 0.08 |
| carbomer 934 | 0.10 |
| DI water | 52.98 |
| triethanolamine | 1.14 |

SPF measurement was performed on a film obtained from the sunscreen composition of Example 32 applied to simulated human skin (Vitro-Skin®, IMS Inc.) using Labsphere UV analyzer 2000S. 20 mg/cm$^2$ of the sunscreen composition was uniformly applied to the Vitro-Skin® followed by immersion of the Vitro-Skin® section in water for 40 mins. SPF, measured after 20 minutes drying of the latex on the Vitro-Skin® section, was 39.

Example 33

A BB cream composition was prepared with the following components and in the amounts (grams) set forth in Table 7 below:

TABLE 7

BB Cream Composition

| Phase | Component | Amount |
|---|---|---|
| A | latex of Ex. 22 | 10 |
| | Glycerine | 7 |
| | DI water | 42.1 |
| | sodium chloride | 1 |
| B | SR 1000[1] | 2 |
| | Silsoft 034[2] | 2 |
| | SF 1540[3] | 4 |
| C | 2-hydroxy-4-methoxybenzophenone | 3 |
| | Avobenzone | 4 |
| | octocrylene | 4 |
| | 2-ethylhexyl salicylate | 4 |
| D | Silsoft 034 | 8.5 |
| | zinc oxide | 2 |
| | BTD-11S2[4] | 5 |
| | BBO-11S2[5] | 0.06 |
| | BRO-11S2[6] | 0.24 |
| | BYO-11S2[7] | 0.6 |
| | Euxyl PE 9010[8] | 0.5 |

[1] Trimethylsiloxy silicate (Momentive Perofrmance Materials Inc.)
[2] Low viscosity alkyl-modified trisiloxane (Momentive Perofrmance Materials Inc.)
[3] 40% solution of polyester silicone copolymer dispersed in cyclopentasiloxane (Momentive Performance Materials Inc.)
[4] Fine white powdery mixture of titanium dioxide and triethoxycaprylylsilane (Kobo Products, Inc.)
[5] Fine black powdery mixture of iron oxides and tristhopyraprylylsilane (Kobo Products, Inc.)
[6] Fine red powdery misture of iron oxides and triethorycaprylylsilane (Kobo Products, Inc.)
[7] Fine yellow powdery mixture of iron oxides and triethopycaprylylsilane (Kobo Products Inc.)
[8] Preservative containing phenoxyethanol and ethylhexylglycerine (Schulke Inc.)

Phases C and D were added to Phase B and heated to 85° C. with stirring until a uniform mixture was obtained. Phase A was also heated to 85° C. and then added to combined Phases B, C and D. The resultant mixture was stirred at high speed to produce a uniform cream mixture. Following the addition of the sodium chloride, the cream was homogenized for 2 min at 11,000 rpm at 85° C. Following homogenization, the mixture was allowed to cool to ambient under slow stirring.

Example 34

A mascara composition was prepared with the components and amounts asset forth below in Table 8:

TABLE 8

Mascara Composition

| Phase | Component | Amount |
|---|---|---|
| A | DI water | 56.8 |
|   | hydroxyethyl cellulose | 0.7 |
|   | black iron oxide | 10 |
|   | triethanolamine | 2 |
|   | latex of Ex. 22 | 10 |
| B | glyceryl stearate | 2.5 |
|   | synthetic beeswax | 10 |
|   | lanolin, anhydrous | 2 |
|   | stearic acid | 5 |
|   | Euxyl PE 9010 (Schulke Inc.)* | 1 |

*Preservative based on phenoxyethanol and ethylhexylglycerin.

The components of Phase B were heated to 85° C. and mixed until a uniform phase was obtained. In a separate vessel, water was heated to 85° C. followed by addition of hydroxyethylcellulose, black iron oxide and the latex of Example 22 under constant stirring to provide Phase A. Phase B was added to Phase A under high speed [rpm?] stirring at 85° C. Mixing was continued until a uniform cream mixture was obtained. The resulting mascara composition was allowed to cool to ambient temperature.

Example 35; Comparative Example 2

Additional mascara compositions were prepared with the components and in the amounts (grams) indicated in Table 9 below.

TABLE 9

Mascara Compositions

| Phase | Components | Ex. 36 | Comp. Ex. 2 |
|---|---|---|---|
| A | DI water | 36.63 | 36.63 |
|   | Polyvinylpyrrolidone K-30 (Sigma-Aldrich) | 2.00 | 2.00 |
|   | hydrophobically modified hydroxyethyl cellulose | 1.00 | 1.00 |
| B | triethanolamine | 1.00 | 1.00 |
|   | methylparaben | 0.30 | 0.30 |
|   | disodium EDTA | 0.10 | 0.10 |
|   | black iron oxide (pre-ground) | 10.00 | 10.00 |
|   | latex of Ex. 22 | 30.24 | — |
|   | silicone acrylate | — | 30.24 |
|   | propylene glycol | 1.13 | 1.13 |
| C | stearic acid | 4 | 4 |
|   | glycerol monostearate | 2 | 2 |
|   | white bleached beeswax | 7 | 7 |
|   | carnauba wax | 3.5 | 3.5 |
|   | hydroxylated lanolin | 1 | 1 |
|   | propylparaben | 0.1 | 0.1 |

The components of Phase A were mixed by hand and stirred at 500 rpm for 30 min at 85° C. Phase B was then added to Phase A. The Phase C components were mixed together, heated to 85°-90° C. and added to the combined A and B phases under stirring at 500 rpm at 85° C. for 5 minutes. The individual compositions were further mixed at 2,000 rpm for 1 minute.

Water resistance of the mascara compositions of Ex. 34 and Comp. Ex. 2 was tested by applying each composition to in-vitro eyelashes (Ardell Runway Lashes). After drying, the eye lashes were dipped into water and hand shaken for 10 seconds. As determined by visual inspection, the mascara composition of Comparative Example 2 exhibited no appreciable water resistance; in contrast to this result, the mascara composition of Example 34 demonstrated significant resistance to water wash-off.

Example 36

Sunscreen compositions were prepared with the components and in the amounts (grams) set forth below in Table 10.

TABLE 10

Sunscreen Compositions

| Component | Ex. 35 | Comp. Ex. 3 |
|---|---|---|
| stearic acid | 3.63 | 3.63 |
| cetyl alcohol | 0.57 | 0.57 |
| dimethicone 5 cst | 14.34 | 24.34 |
| latex of Ex. 15 | 10.00 | — |
| C12-15 alkylbenzoate | 5.00 | 5.00 |
| caprylic capric triglyceride | 5.00 | 5.00 |
| octylmethoxycinnamate | 2.50 | 2.50 |
| octylsalicylate | 1.67 | 1.67 |
| oxybenzone | 2.00 | 2.00 |
| avobenzone | 1.00 | 1.00 |
| tetrasodium EDTA | 0.08 | 0.08 |
| carbomer 981 | 1.00 | 1.00 |
| DI water | 52.97 | 52.97 |
| triethanolamine | 1.14 | 1.14 |

Water resistance was determined by measuring the SPF of each sunscreen composition before and after the water wash-off test. Water resistance of the sunscreen compositions was tested by immersing separate in-vitro skin sections (Vitro-Skin®, IMS Inc.) to which each sunscreen composition was applied in water for 40 minutes followed by drying.

The results of the water wash-off testing are set forth in Table 11 below:

TABLE 11

Results of Water Wash-off Test

| | Example 37 | | Comparative Example 3 | |
|---|---|---|---|---|
| | Before Immersion | After Immersion | Before Immersion | After Immersion |
| SPF | 35 ± 3.8 | 38 ± 7.6 | 28 ± 2.5 | 17 ± 6.8 |

As these data show, the sunscreen of Example 35 demonstrated not only a higher SPF than that of the sunscreen of Comp. Ex. 3, following immersion the SPF of Example 35 sunscreen increased whereas the SPF of the sunscreen of Comp. Ex. 3 following immersion fell by nearly 40 percent compared to its pre-immersion level.

While the disclosure has been described with reference to a preferred embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from essential scope thereof. Therefore, it is intended that the disclosure not be limited to the particular embodiment disclosed as the best mode contemplated for carrying out this disclosure, but that the disclosure will include all embodiments falling within the scope of the appended claims.

The invention claimed is:

1. A hydrophobic hybrid organosiloxane nano latex comprising the copolymerizate of:
   (a) organosiloxane monomer consisting of the general formula $M_aM^v{}_bD_cD^v{}_d$
   wherein:
   $M=R_1R_2R_3SiO_{1/2}$,
   $M^v=R_4R_5R_uSiO_{1/2}$,
   $D=R_6R_7SiO_{2/2}$, and
   $D^v=R_8R_uSiO_{2/2}$,
   in which each of $R_1$, $R_2$, $R_3$, $R_4$, $R_5$, $R_6$, $R_7$, and $R_8$ is independently selected from hydrogen, a hydroxyl group, or a hydrocarbyl group having up to 100 carbon atoms, but containing no heteroatoms; $R_u$ is a; free-radical polymerizable group; subscripts a, b, c, and d, each independently range from 0 to 10,000 subject to the limitation that b+d is at least 1; and,
   (b) monomer possessing a group which is free-radical copolymerizable with group $R_u$ of organosiloxane monomer (a) and, wherein the copolymerizate has a particle size ranging from 10 to 990 nm.

2. The hydrophobic hybrid organosiloxane nano latex of claim 1 in the form of a film having a contact angle of at least 50°.

3. The hydrophobic hybrid organosiloxane nano latex of claim 1 in the form of a film having a contact angle of at least 60°.

4. The hydrophobic hybrid organosiloxane nano latex of claim 1 in the form of a film having a contact angle of at least 70°.

5. The hydrophobic hybrid organosiloxane nano latex of claim 1 wherein in organosiloxane monomer (a), each $R_u$ is independently an ethylenically unsaturated group selected from Formulas I, II(a), II(b) and II(c):

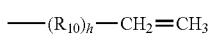
Formula I

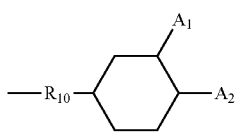
Formula II(a)

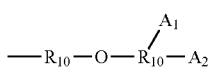
Formula II(b)

Formula II(c)

wherein:
each $R_{10}$ is independently selected from linear or branched alkyl groups of up to 10 carbon atoms; $A_1$ and $A_2$ each independently is a group capable of undergoing free radical addition reaction; and, subscripts p, q and r each independently range from 0 to 100.

6. The hydrophobic hybrid organosiloxane nano latex of claim 5 wherein $A_1$ and $A_2$ each independently is a group of formula III:

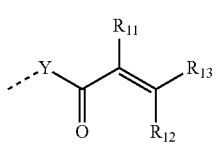
Formula (III)

wherein $R_{11}$, $R_{12}$ and $R_{13}$ each independently is hydrogen or hydrocarbyl group of up to 5 carbon atoms, Y is absent or is a linking group selected from the group consisting of divalent aliphatic, cycloaliphatic or aromatic hydrocarbon groups of 2 to 16 carbons.

7. The hydrophobic hybrid organosiloxane nano latex of claim 1 wherein monomer (a) is selected from the group consisting of vinyl functional silicone, hydroxy functional silicone acrylates, organo modified silicone (meth)acrylates, organo modified silicone acrylamides, organo modified silicone (meth)acrylamides, their derivatives and mixtures thereof.

8. The hydrophobic hybrid organosiloxane nano latex of claim 7 which is the copolymerizate of monomer (a) and at least two monomers (b).

9. The hydrophobic hybrid organosiloxane nano latex of claim 1, wherein monomer (b) is selected from the group consisting of acrylic acid, methacrylic acid, their esters, their amide derivatives and mixtures thereof.

10. The hydrophobic hybrid organosiloxane nano latex of claim 1 wherein monomer (b) is selected from the group consisting of methyl methacrylate, butyl acrylate, propyl acrylate, tert-butyl methacrylate, N,N-dimethylacrylamide, N-isopropyl acrylamide, 2-ethylhexyl acrylate, cyclohexyl acrylate, vinlyl acrylate, allyl acrylate, hydroxyethyl acrylate, perfluoroethyl acrylate, isobornyl acrylate, lauryl methacrylate, lauryl arylate, cetyl methacrylate, behenyl acrylate, phenoxyethyl acrylate, tetraethylene glycol diacrylate, tripropylene glycol diacrylate, acrylamide, methacrylamide, acrylated silane, methacrylated silane, methacryloxyl silane, 2-hydroxyethyl methacrylate, 3-[tris(trimethylsiloxy)silyl] propyl methacrylate, acrylate and methacrylate functional carbosilanes, hexafunctional urethane acrylates, dipentaerythritol pentaacrylate, ethoxylated pentaerythritol tetraacrylate, di-trimethylolpropane tetraacrylate, pentaerythritol triacrylate, trimethylolpropane triacrylate, ethoxylated trimethylolpropane triacrylate, butanediol diacrylate, tripropylene glycol diacrylate, trimethylolpropane trimethacrylate, oligofunctional urethane acrylates, tetraacrylate monomer, polyester acrylate oligomers, and combinations thereof.

11. The hydrophobic hybrid organosiloxane nano latex of claim 1 wherein the particle size of the copolymerizate is from 30 to 750 nm.

12. The hydrophobic hybrid organosiloxane nano latex of claim 1 wherein the particle size of the copolymerizate is from 50 to 500 nm.

13. The hydrophobic hybrid organosiloxane nano latex of claim 1 wherein the content of copolymerizate is from 0.1 to 40 weight percent of the latex.

14. The hydrophobic hybrid organosiloxane nano latex of claim 1 wherein the content of copolymerizate is from 0.1 to 35 weight percent of the latex.

15. The hydrophobic hybrid organosiloxane nano latex of claim 1 wherein the viscosity is from 0.1 to about 250 cps.

16. The hydrophobic hybrid organosiloxane nano latex of claim 1 wherein the viscosity is from 0.5 to about 230 cps.

17. The hydrophobic hybrid organosiloxane nano latex of claim 1 wherein the viscosity is from 1 to about 200 cps.

18. A personal care composition comprising a film-forming amount of hydrophobic hybrid organosiloxane nano latex of claim 1.

19. The personal care composition of claim 18 wherein the film obtained from the hydrophobic hybrid organosiloxane nano latex has a contact angle of at least 50°.

20. The personal care composition of claim 18 wherein the film obtained from the hydrophobic hybrid organosiloxane nano latex has a contact angle of at least 60°.

21. The personal care composition of claim 18 wherein the film obtained from the hydrophobic hybrid organosiloxane nano latex has a contact angle of at least 70°.

22. The personal care composition of claim 18 which is selected from the group consisting of deodorants, antiperspirants, antiperspirant/deodorants, stick and roll-on products, skin lotions, moisturizers, toners, cleansing products, styling gels, hair dyes, hair color products, hair straighteners, nail polish, nail polish remover, sunscreens, anti-aging products, lipsticks, lip balms, lip glosses, foundations, face powders, eye liners, eye shadows, blushes, makeup, beauty balms, mascaras, moisturizing preparations, foundations, concealers, body and hand preparations, skin care preparations, face and neck preparations, fragrance preparations, soft focus applications, night and day skin care preparations, tanning preparations, hand liquids, non-woven applications for personal care, baby lotions, facial cleansing products, hair cuticle coats, gels, foam baths, body washes, scrubbing cleansers, controlled-release personal care products, hair shampoos, hair conditioners, hair sprays, skin care moisturizing mists, skin wipes, pore skin wipes, pore cleaners, blemish reducers, skin exfoliators, skin desquamation enhancers, skin towelettes and cloths, depilatory preparations, personal care lubricants, nail coloring preparations and drug delivery systems for topical application of medicinal compositions that are to be applied to the skin.

23. The personal care composition of claim 22 wherein the film obtained from the hydrophobic hybrid organosiloxane nano latex has a contact angle of at least 50°.

24. The personal care composition of claim 22 wherein the film obtained from the hydrophobic hybrid organosiloxane nano latex has a contact angle of at least 60°.

25. The personal care composition of claim 22 wherein the film obtained from the hydrophobic hybrid organosiloxane nano latex has a contact angle of at least 70°.

26. A hydrophobic hybrid organosiloxane nano latex consisting essentially of the copolymerizate of:
(a) organosiloxane monomer consisting of the general formula $M_a M^v{}_b D_c D^v{}_d$
wherein:
$M=R_1R_2R_3SiO_{1/2}$,
$M^v=R_4R_5R_uSiO_{1/2}$,
$D=R_6R_7SiO_{2/2}$, and
$D^v=R_8R_uSiO_{2/2}$,
in which each of $R_1$, $R_2$, $R_3$, $R_4$, $R_5$, $R_6$, $R_7$, and $R_8$ is independently selected from hydrogen, a hydroxyl group, or a hydrocarbyl group having up to 100 carbon atoms, but containing no heteroatoms; $R_u$ is a; free-radical polymerizable group; subscripts a, b, c, and d, each independently range from 0 to 10,000 subject to the limitation that b+d is at least 1; and,
(b) monomer possessing a group which is free-radical copolymerizable with group $R_u$ of organosiloxane monomer (a).

27. A hydrophobic hybrid organosiloxane nano latex comprising the copolymerizate of:
(a) organosiloxane monomer consisting of the general formula $M_a M^v{}_b D_c D^v{}_d$
wherein:
$M=R_1R_2R_3SiO_{1/2}$,
$M^v=R_4R_5R_uSiO_{1/2}$,
$D=R_6R_7SiO_{2/2}$, and
$D^v=R_8R_uSiO_{2/2}$,
in which each of $R_1$, $R_2$, $R_3$, $R_4$, $R_5$, $R_6$, $R_7$, and $R_8$ is independently selected from hydrogen, a hydroxyl group, or a hydrocarbyl group having up to 100 carbon atoms, but containing no heteroatoms; $R_u$ is independently an ethylenically unsaturated group selected from Formulas I, II(a), II(b) and II(c):

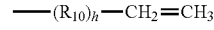

Formula I

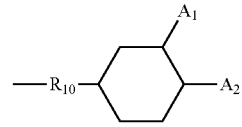

Formula II(a)

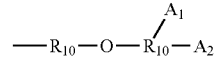

Formula II(b)

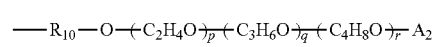

Formula II(c)

wherein:
each $R_{10}$ is independently selected from linear or branched alkyl groups of up to 10 carbon atoms; $A_1$ and $A_2$ each independently is a group capable of undergoing free radical addition reaction; and, subscripts p, q and r each independently range from 0 to 100;
subscripts a, b, c, d, each independently range from 0 to 10,000 subject to the limitation that b+d is at least 1; and,
(b) monomer possessing a group which is free-radical copolymerizable with group $R_u$ of organosiloxane monomer (a) and, wherein the copolymerizate has a particle size ranging from 10 to 990 nm.

* * * * *